United States Patent [19]

Stummer et al.

[11] 4,169,035
[45] Sep. 25, 1979

[54] ELECTROLYTIC CELL FOR TREATMENT OF WATER SOLUTIONS

[75] Inventors: Franz Stummer; Jorge Miller, both of Nöham, Fed. Rep. of Germany

[73] Assignee: Firma Hans Einhell GmbH Industriegelande, Landau, Fed. Rep. of Germany

[21] Appl. No.: 847,101

[22] Filed: Oct. 31, 1977

[30] Foreign Application Priority Data

Oct. 29, 1976 [DE] Fed. Rep. of Germany ....... 2649649

[51] Int. Cl.² .................. C25B 9/00; C25B 11/02; C25B 15/08
[52] U.S. Cl. ............................ 204/260; 204/263; 204/261
[58] Field of Search ............. 204/275, 263, 149, 151, 204/109, 260, 261, 222, 273

[56] References Cited

U.S. PATENT DOCUMENTS

| | | | |
|---|---|---|---|
| 2,154,052 | 4/1939 | Rolande | 204/275 X |
| 3,378,479 | 4/1968 | Colvin et al. | 204/275 X |
| 3,767,542 | 10/1973 | Carlson | 204/261 X |
| 4,046,663 | 9/1977 | Fleet et al. | 204/149 X |
| 4,046,663 | 9/1977 | Fleet et al. | 204/149 X |
| 4,049,512 | 9/1977 | Tolle, Jr. | 204/275 |

*Primary Examiner*—John H. Mack
*Assistant Examiner*—D. R. Valentine
*Attorney, Agent, or Firm*—Stevens, Davis, Miller & Mosher

[57] ABSTRACT

An electrolytic cell for the treatment of aqueous solutions, comprising a closed container with an inlet aperture and an outlet orifice for water flowing through the container having at least two electrodes positioned within said container which can be connected to the positive and negative poles of a direct current source, at least one electrode being constituted of an elastically deformable electrically conductive body.

2 Claims, 4 Drawing Figures

ELECTROLYTIC CELL FOR TREATMENT OF WATER SOLUTIONS

The invention relates to an electrolytic cell for the treatment, particularly the purification and sterilization, of aqueous solutions. In particular, it relates to a multi-pole electrolytic cell which can be used for the most widely diverse types of treatment and which consists essentially of a closed container with a bottom water inlet aperture and an upper water outlet orifice and also at least two electrodes which can be connected to the positive and negative poles of a direct current source.

All manner of types of electrolytic cells for the treatment, particularly for the purification and sterilizing of aqueous solutions, particularly water, are already known. With these known electrolytic cells, it is possible electrolytically to eliminate from the aqueous solutions which are to be treated any undesired suspended and dissolved impurities, by the use of electrodes consisting of iron, aluminum, copper, silver, platinum, carbon or the like. However, while such electrolytic cells are being used, problems arise which have the most widely diverse origins.

With regard to the electrolysis of aqueous solutions, not only oxygen but also other products of oxidation are formed on the anode while in addition to hydrogen, particularly in the case of hard water, also calcium and other alkaline earth metal carbonates are formed on the cathode. The carbonates rapidly deposit on the cathode in the form of a coating and prevent the flow of electric current. With increasing thickness of the deposits on the cathode, the flow of electric current and also the throughflow of water through the electrolytic cell become more and more inhibited, i.e., the actual function of the electrolytic cell is increasingly diminished.

In order to avoid this, such an electrolytic cell must be constantly monitored and correspondingly maintained (cleaned), which involve high costs in labor and time. Indeed, it is possible by periodically reversing the polarity in the flowing current to remove the undesired deposits of calcium and other alkaline earth metals from the cathode, but in practice it has been found that this only leads to increased corrosion of the cathode and the problem is further intensified. Also, there have been attempts to keep the electrodes, particularly the cathode, mechanically clean and free of undesired deposits by means of brushes or other movable parts. However, all these systems are highly susceptible to trouble due to the differing rates of flow and differing degree of dirt in the water flowing through the cell and due to the considerable mechanical wear and tear occasioned by mechanical cleaning. Furthermore, these mechanical cleaning systems entail considerable noise, which is likewise undesirable, particularly in large industrial installations.

Therefore, the object of the invention is to avoid deposits forming on the electrodes, particularly on the cathode, of an electrolytic cell which inhibit the flow of electric current and the flow of water passing through the electrolytic cell.

According to the invention, this object is achieved in that the electrode(s), particularly the cathode, in the electrolytic cell forms (form) in itself an elastically movable structure. At the same time, it is immaterial what specific form this (these) per se elastically movable structure has (have), so long as it is ensured that its (their) surface can be elastically deformed by bending and/or torsion, either under the influence of the aqueous solution flowing through the electrolytic cell or under the influence of additional means giving rise to a forced elastic movement of the electrically conductive body.

The object of the invention is an electrolytic cell for the treatment of aqueous solutions and consisting of a closed container with an inlet and an outlet for the water flowing through the container, and having at least two electrodes which can be connected to the positive and negative poles of a direct current source, the electrolytic cell according to the invention being characterized in that at least one electrode constitutes an electrically conductive body which can in itself be elastically deformed, preferably by bending and/or torsion.

The electrode(s) which may be fixed at one or both ends may take the form of an elastically deformable thread, wire or strip or may take the form of an elastic preferably multi-arm conical coil spring which is set in motion, i.e., caused to perform elastic oscillations, by the turbulence of flow in the aqueous solution (hereinafter referred to for sake of simplicity always as "water") flowing through the container. It is also possible to produce these elastic oscillations of the electrode by mechanical, magnetic or electromagnetic means, for example by means of a body of flow, by means of a motor, by means of permanent magnets or electromagnets.

The result of these elastic deformations of the electrode, particularly of the cathode, is that the electrode or cathode is constantly flexion and torsion stressed so that in this way the formation of undesired deposits on the electrode or cathode is prevented.

According to a preferred development of the invention, the electrolytic cell for the treatment of aqueous solutions consists essentially of a two-part preferably conical-cylindrical housing with a bottom inlet aperture and a top outlet orifice for the water flowing through the container. Inside the housing there are, from the outside inwards, a grid anode adapted to the shape of the housing, a diaphragm disposed parallel therewith and a cathode having good spring properties and constructed preferably as a multi-arm spiral. Anode and cathode are preferably constructed in the lower portion of the electrolytic cell as a flat ring and both are led out through interposed sealing-insulating discs, between the flanges of the upper part and lower part of the housing, in order to make the necessary electrical connections. Inside the preferably multi-arm spiral cathode and without making direct contact therewith, there is in the center of the electrolytic cell a flow body having driving vanes, constructed preferably as a rotor and preferably mounted at top and bottom inside the electrolytic cell. This flow body preferably has a conical form tapering preferably towards the outlet from the electrolytic cell. It may however also have any other desired suitable form and rotate or not rotate.

The flow body located inside the cathode and constructed as a rotor has the function of attuning the rate of water throughflow to the cathode so that the latter can absorb sufficient motional energy. By reason of its rotation caused by the water flowing through the electrolytic cell, it prevents coarse dirt such as for example leaves, hair and the like, clinging to the cathode in that its vanes pass such coarse matter spirally along the cathode towards the outlet end of the electrolytic cell.

In contrast to the known electrolytic cells, the following technical advantages are achieved by the electrolytic cell according to the invention:

(a) by disposing the anode and diaphragm directly on the inner periphery of the cell housing, maximum diaphragm surface is available for carrying out the electrolysis;

(b) the electrical connections for the electrodes, particularly the anode and cathode, can be led out under fully insulated conditions without any considerable technical complication, so that the current applied between anode and cathode can only flow through the diaphragm, i.e., no non-operative currents are formed between the connecting contacts inside the electrolytic cell;

(c) in the electrolytic cell according to the invention, it is possible to use only one cathode and only one anode, the electrical connections of both electrodes being outside the cell;

(d) by reason of the small distance between the active surfaces of anode and cathode and by reason of the large area diaphragm, the electrolytic cell can be operated with minimal electrical voltage, i.e., with minimal electric power;

(e) the electrolytic cell according to the invention, by reason of its special construction and special shape, offers only very minimal resistance to the flow of water and dirt;

(f) inside the electrolytic cell according to the invention there are no parts which rub mechanically on one another and which therefore suffer rapid wear and tear;

(g) the preferred use of a conical-cylindrical shape in the electrolytic cell according to the invention renders the diaphragm very form-stable and prevents lateral deflection of the spiral cathode in the direction of the diaphragm, since under traction loading, the spiral cathode tapers towards the outlet end, so that despite the small distance between spiral cathode and diaphragm, collision between the two devices can be reliably avoided;

(h) the conical-cylindrical form of the cathode, tapering towards the outlet end of the cell ensures that the particularly aggressive gaseous oxidizing media arising inside the anode portion defined on the one hand by the diaphragm and the cell wall on the other rise vertically upwardly and are therefore eliminated from the diaphragm, so that the diaphragm does not have to be additionally protected but may be protected in exceptional cases from less aggressive fluid oxidizing media, with a coating material which need not be form-stable and which is only suitable for traction loading;

(i) the electrolytic cell according to the invention consists of only a few simply shaped and easily made parts and can also be quickly and easily assembled, since in order to produce the preferred embodiment of the invention, only rotationally symmetrical conical injection molded parts are used, the injection molding tools needed for the purpose are uncomplicated and the parts are easily molded;

(j) the electrolytic cell according to the invention can be operated in any desired position, operation in a vertical position being however preferred.

Further objects, advantages and features of the invention will become evident from the ensuing description in which the invention is explained in greater detail with reference to preferred forms of embodiment illustrated in the accompanying drawings in which identical parts are provided with identical reference numerals, and in which.

Figure 1:
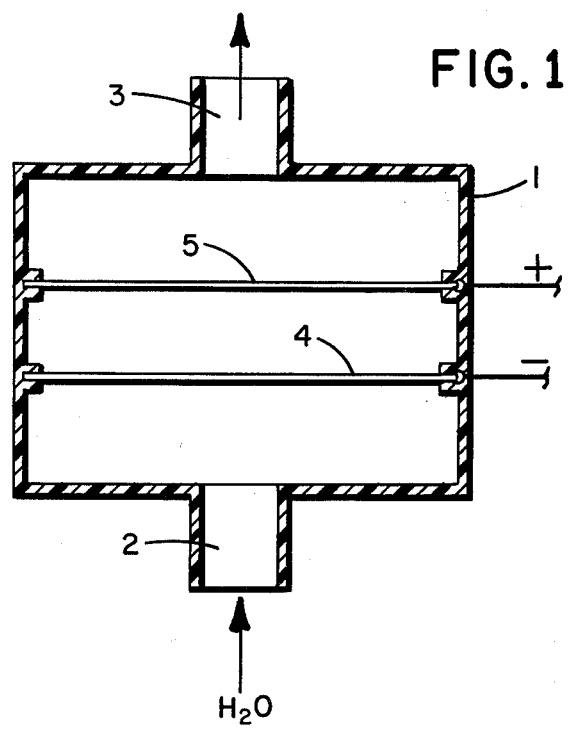
FIG. 1 is a diagrammatic view of a simplified embodiment of the electrolytic cell according to the invention.
Figure 3:
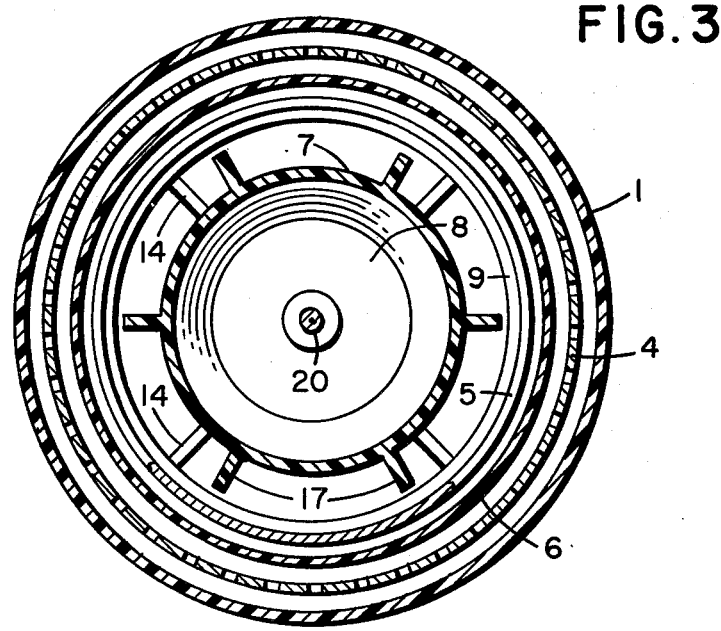
FIG. 3 is a sectional view of the embodiment of FIG. 2 taken on line 3—3 of FIG. 2.

The diagram of the electrolytic cell according to the invention, as shown in FIG. 1, consists of a preferably cylindrical container 1 with a bottom inlet 2 and a top outlet 3 for the water flowing through the cell and two in elastically deformable electrodes 4 and 5 which may be connected to a direct current source (not shown).

Under the influence of the water flowing through the electrolytic cell, the two electrodes 4 and 5 are caused to vibrate which prevent deposits forming on the electrodes during the execution of electrolysis. The vibrations of the electrodes can be produced directly by the through-flowing water (Karman eddying) or indirectly by turbulence, permanent magnets or electromagnets.

Figure 2:
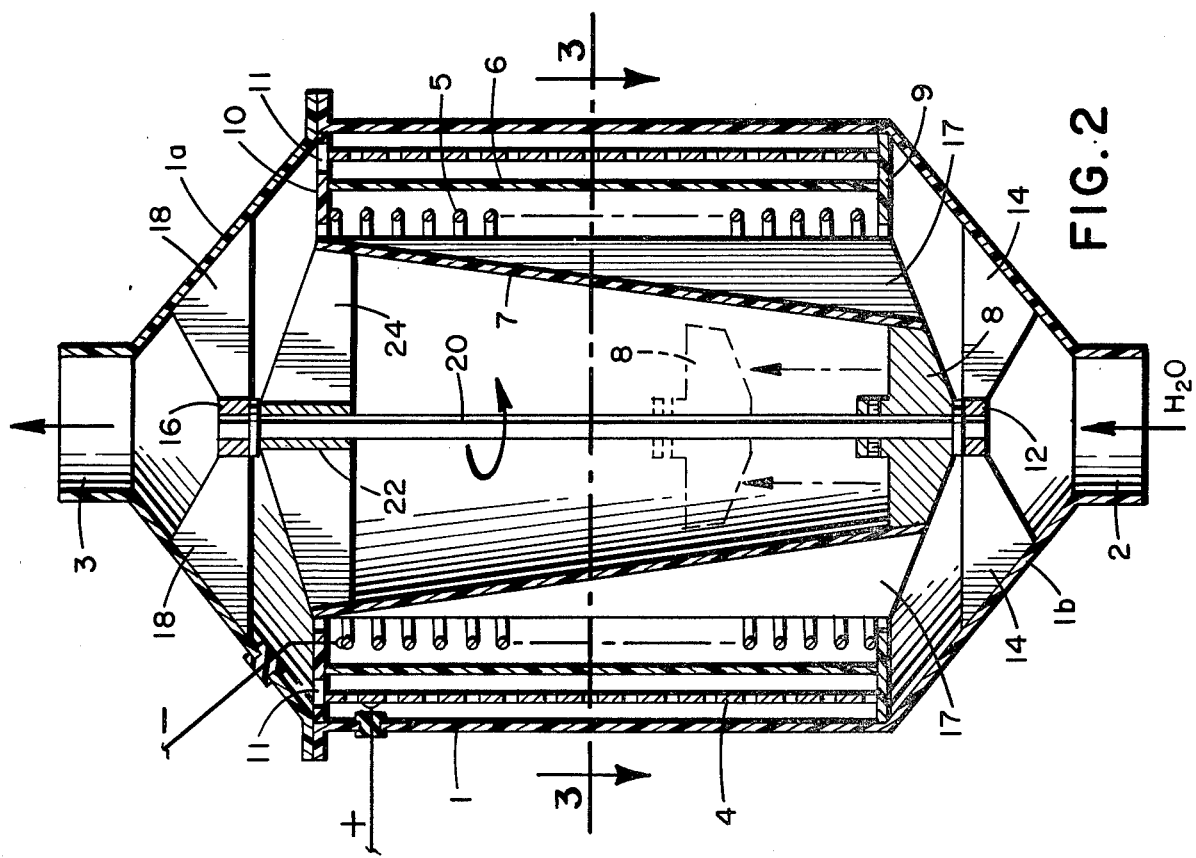
FIG. 2 is a vertical sectional view of a preferred embodiment of the electrolytic cell according to the invention.

A preferred embodiment of the electrolytic cell according to the invention which is shown in FIG. 2 consists of a cylindrical housing 1 with conical outlet and inlet portions 1a and 1b, respectively with a bottom inlet aperture 2 and an upper outlet orifice 3. Inside the housing, in sequence from the outside inwards, there are a perforated grid anode 4 adapted to the shape of the housing, a permeable diaphragm 6 and a helical spring cathode 5 having good vibration properties. The anode and the cathode are supported at the bottom portion of the electrolytic cell as a flat ring, electrically insulated from the housing and are connected to a direct current electric source. The anode portion defined by the diaphragm 6 and the cylindrical walls of the housing, with the grid anode 4 dispostied therebetween is closed at the top by insulating ring 10 which has slots 11 to allow escape of the oxidizing gases which form inside the anode chamber. Concentric with the helical cathode 5, in the center of the electrolytic cell 1, there is, mounted a rotor 7 in bearing 12 at the bottom and in bearing 16 at the top. The rotor 7, having drive vanes 17, is secured to shaft 20 by a sleeve 22 and spider structure 24 and does not come directly into contact with the helical spiral cathode 5. The bearing 12 is supported by a spider structure 14 positioned on the conical wall of inlet housing 1b. Bearing 16 is supported by a spider structure positioned on the conical wall of the outlet housing 14. Raising the valve 8 to a position such as shown in dash lines allows some of the water to flow up the inside of shell 7, thereby reducing the rate of flow around the spring 5 and thus reducing the rate of vibration.

Figure 4:
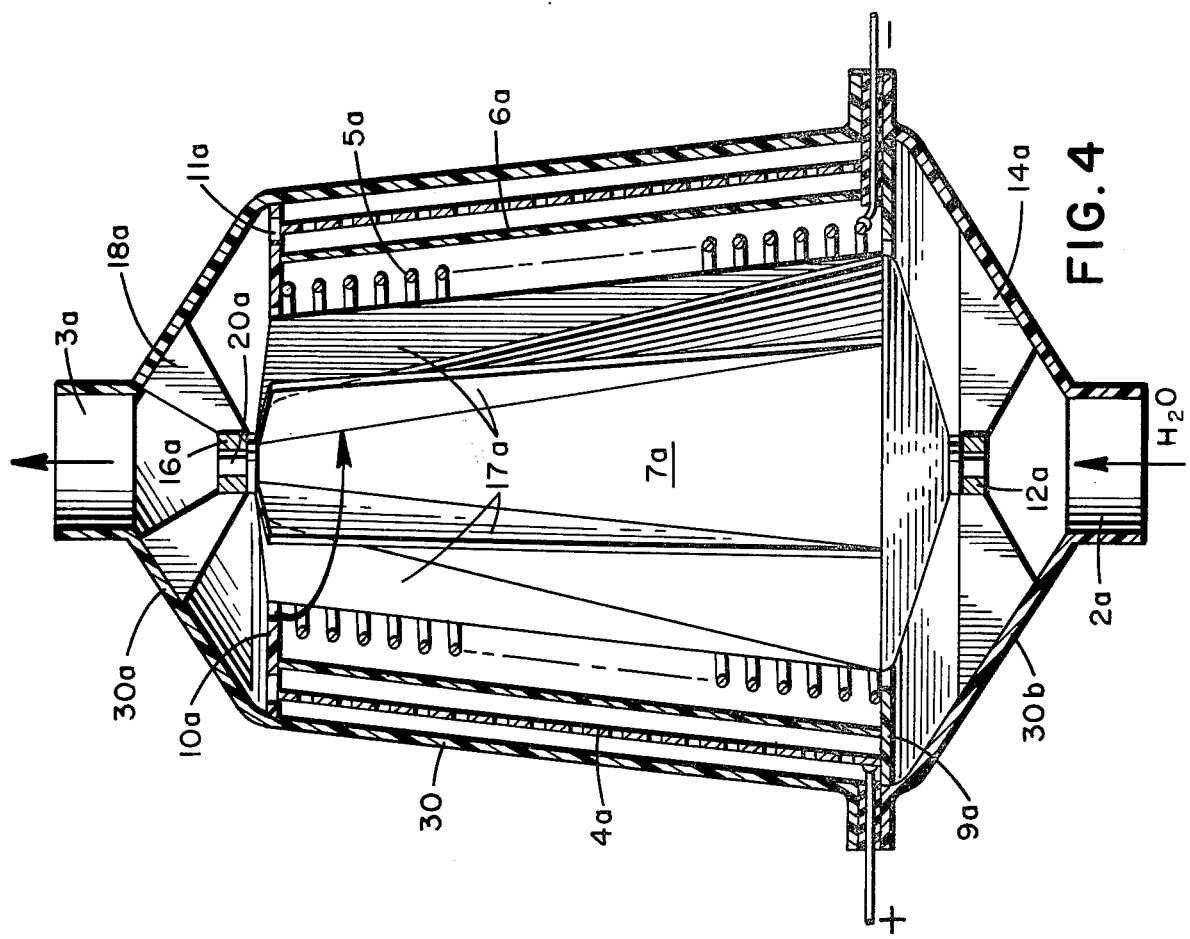
FIG. 4 is a vertical sectional view of another preferred embodiment of the electrolytic cell according to the invention.

The other preferred embodiment of the electrolytic cell according to the invention which is shown in FIG. 4 is substantially of the same construction as the electrolytic cell according to FIG. 2, although in this case the rotor 7a disposed in the center of the spiral cathode tapers inwardly towards the water outlet aperture 3.

The following materials are examples of those which may be used for constructing the electrolytic cell according to the invention, as is illustrated by way of example in FIGS. 1 to 4 of the accompanying drawings:

The anode 4 consists preferably of platinized titanium or platinized niobium in the form of a grid (e.g. of expanded metal), but it may also consist of any other metal taken from the group of platinum metals which is resistant to corrosion, or it may consist of graphite or carbon or a metal oxide. The anode may be solid or it may take the form of a grid (expanded metal).

The cathode 5 may consist of any desired electrically conductive material, preferably a metal such as stainless steel, copper and the like.

The diaphragm 6 may consist for example of porous porcelain, a microporous synthetic plastics material such as a polyolefin, polyvinyl chloride, cellulose nitrate and an ion exchanger resin.

If the porous diaphragm 6 is sensitive to the oxidizing gases or liquids forming inside the anode portion, then it may be screened (protected) by a coating of an electrically non-conductive material such as a plastic.

Possible materials for the manufacture of the electrolytic cell housing 1, the inlet 2, the outlet 3 for the throughflowing water and for the rotor 7 are electrically non-conductive materials such as plastics, porcelain, glass, hard rubber, concrete and the like.

The invention has indeed been explained in greater detail hereinabove with reference to preferred forms of embodiment, but it goes without saying, to a man skilled in the art, that it is in no way limited to these embodiments which may be altered and modified in many respects without thereby departing from the framework of the present invention. For example, the cell need not have a cylindrical cross-section; instead, it may be elliptical, hexagonal or the like. The cell can be so constructed that the water to be treated passes through it in one direction or the other or alternately in both directions. The preferred conical form of electrolytic cell can taper both in the direction of the flowing water and also against the direction of the flowing water. That also applies to the flow body disposed inside the electrolytic cell and which can be operated in a vertical attitude as a weightforce suspended rotor or in any desired attitude by applying an elastic force acting on the rotor against the direction of flow. Consequently, it is readily possible to stabilize the rate of flow of the water in the cathode zone by varying the throughflow crosssection according to different water throughputs. It is also possible to provide a fixed or automatically adjustable by-pass inside the flow body which is constructed as a rotor. Furthermore, the electrolytic cell can be adapted to various water throughputs by a flow body, the height of which is rigidly adjustable.

It is also possible for example to dispose two diaphragms one inside the other in order to increase the concentration of oxidizing agent inside the anode portion, so that this can be passed out into the throughflowing water in highly concentrated form through the outlet slots in the anode part.

There are manifold possibilities for constructing the electrodes just as there are many ways in which the elastic movements can be brought about, for example mechanically, magnetically or electrically. For example, permanent magnets may be disposed on the rotor blades and a correspondingly magnetizable electrode can be set in motion thereby. The elastically deformable electrode may also be provided with a magnetic plate. It is also possible for the elastic oscillations of the cathode to be produced by magnetic or mechanical means or for the cathode to be caused to rotate. Furthermore, for example the height of the flow body which is constructed as a suspended rotor may, by means of suitable devices, be used to monitor the flow of water within the electrolytic cell or - if the housing consists of a transparent material, it may be used as a flow meter. It is also possible to incorporate a small permanent magnet generator at one mounting of the rotor, and to utilize the resultant electrical energy for measuring or control purposes.

The rotor disposed in the interior of the cell can also be constructed as a rotating brush. Furthermore, the natural frequency of the elastic system, i.e., of the spiral electrode(s) inside the electrolytic cell may be modified in any desired manner, i.e. reduced, by the provision of a weight which is preferably constructed as a flow body.

What is claimed is:

1. An electrolytic cell, consisting of a two-part conical-cylindrical walled housing having a bottom inlet aperture and an upper outlet orifice for throughflowing water, a grid anode adapted to the wall of the housing and located inside the housing, a diaphragm disposed parallel thereto, an elastically movable cathode disposed interiorly of the diaphragm and a conical flow body mounted adjacent the bottom inlet aperture and upper outlet orifice inside the housing and inside the cathode constructed as a rotor having drive blades out of contact with said cathode, said body being tapered towards the outlet orifice.

2. An electolytic cell consisting of a conical-cylindrical walled housing having a bottom inlet aperture and an upper outlet orifice for throughflowing water, a grid anode adapted to the wall of the housing and located inside the housing, a diaphragm disposed parallel to and interiorly of the grid anode, an elastically movable cathode disposed interiorly of the diaphragm, a conical flow body mounted adjacent the bottom inlet aperture and upper outlet orifice inside the housing and inside the cathode, said conical flow body being tapered towards the water inlet aperture and at the narrowest end of said conical flow body and adjustable along an axis of said conical flow body a compensating valve for attuning the water throughflow rate to the mechanical properties of the cathode.

* * * * *